United States Patent [19]

Bianco

[11] Patent Number: 4,855,942
[45] Date of Patent: Aug. 8, 1989

[54] PEDOMETER AND/OR CALORIE MEASURING DEVICE AND METHOD

[75] Inventor: Frank J. Bianco, Pembroke Pines, Fla.

[73] Assignee: Elexis Corporation, Miami, Fla.

[21] Appl. No.: 113,745

[22] Filed: Oct. 28, 1987

[51] Int. Cl.⁴ .................... G06F 15/42; G01C 21/00
[52] U.S. Cl. .................... 364/561; 235/105; 364/413.11; 364/413.01; 368/10; 377/24.2
[58] Field of Search ........... 364/410, 413, 417, 561; 364/413.01, 413.02, 413.03, 413.04, 413.11; 377/16, 24.2; 368/10, 165; 128/690, 707, 782, 689; 340/323 R; 200/182; 235/105

[56] References Cited

U.S. PATENT DOCUMENTS

| | | | |
|---|---|---|---|
| 3,797,010 | 3/1974 | Adler et al. | 377/24.2 |
| 3,871,170 | 3/1975 | Bergey | 368/69 |
| 4,053,755 | 10/1977 | Sherrill | 364/561 |
| 4,100,401 | 7/1978 | Tutt et al. | 364/413 |
| 4,101,071 | 7/1978 | Brejnik et al. | 364/415 |
| 4,108,166 | 8/1978 | Schmid | 128/710 |
| 4,112,928 | 9/1978 | Putsch | 128/707 |
| 4,144,568 | 3/1979 | Hiller et al. | 364/413 |
| 4,192,000 | 3/1980 | Lipsey | 364/410 |
| 4,202,350 | 4/1980 | Walton | 128/690 |
| 4,216,956 | 8/1980 | Yamamura et al. | 340/323 R |
| 4,220,996 | 9/1980 | Searcy | 364/561 |
| 4,223,211 | 9/1980 | Allsen et al. | 377/24.2 |
| 4,322,609 | 3/1982 | Kato | 235/105 |
| 4,367,752 | 1/1983 | Jimenez et al. | 128/782 |
| 4,380,802 | 4/1983 | Segar et al. | 364/413 |
| 4,387,437 | 6/1983 | Lowrey et al. | 364/561 |
| 4,434,801 | 3/1984 | Jiminez et al. | 364/415 |
| 4,525,074 | 6/1985 | Murakami | 368/10 |
| 4,566,461 | 1/1986 | Lubell et al. | 364/417 |
| 4,578,769 | 3/1986 | Frederick | 364/561 |
| 4,687,340 | 8/1987 | Havel | 368/10 |
| 4,741,001 | 4/1988 | Ma | 377/24.2 |
| 4,771,394 | 9/1988 | Cavanagh | 235/105 |

FOREIGN PATENT DOCUMENTS 2190773  11/1987  United Kingdom ............ 235/105

Primary Examiner—Parshotam S. Lall
Assistant Examiner—Kevin J. Teska
Attorney, Agent, or Firm—Lowe, Price, LeBlanc, Becker & Shur

[57] ABSTRACT

The number of calories consumed by subject performing an exercise routine is approximated with a computer having a predetermined cycle time during which the distance travelled by the subject is determined. Indications of the subject weight, sex and age are entered into a memory of the computer to cause the computer to compute and store an indication of the number of calories the subject burns in traversing a predetermined distance during the computer cycle time. The calories consumed by the subject during the cycle time are calculated from the stored indication and the distance travelled during the cycle time. The indications of calculated consumed calories are accumulated over several consecutive cycle times. To determine distance travelled, signals from a pedometer are combined in the computer with a subject's stored stride length signal. The pedometer includes a mercury switch having an envelope containing contacts and a mercury globule for selectively wetting and bridging the contacts in response to cyclic motion of the subject. The entire structure is mounted in a watch case.

42 Claims, 4 Drawing Sheets

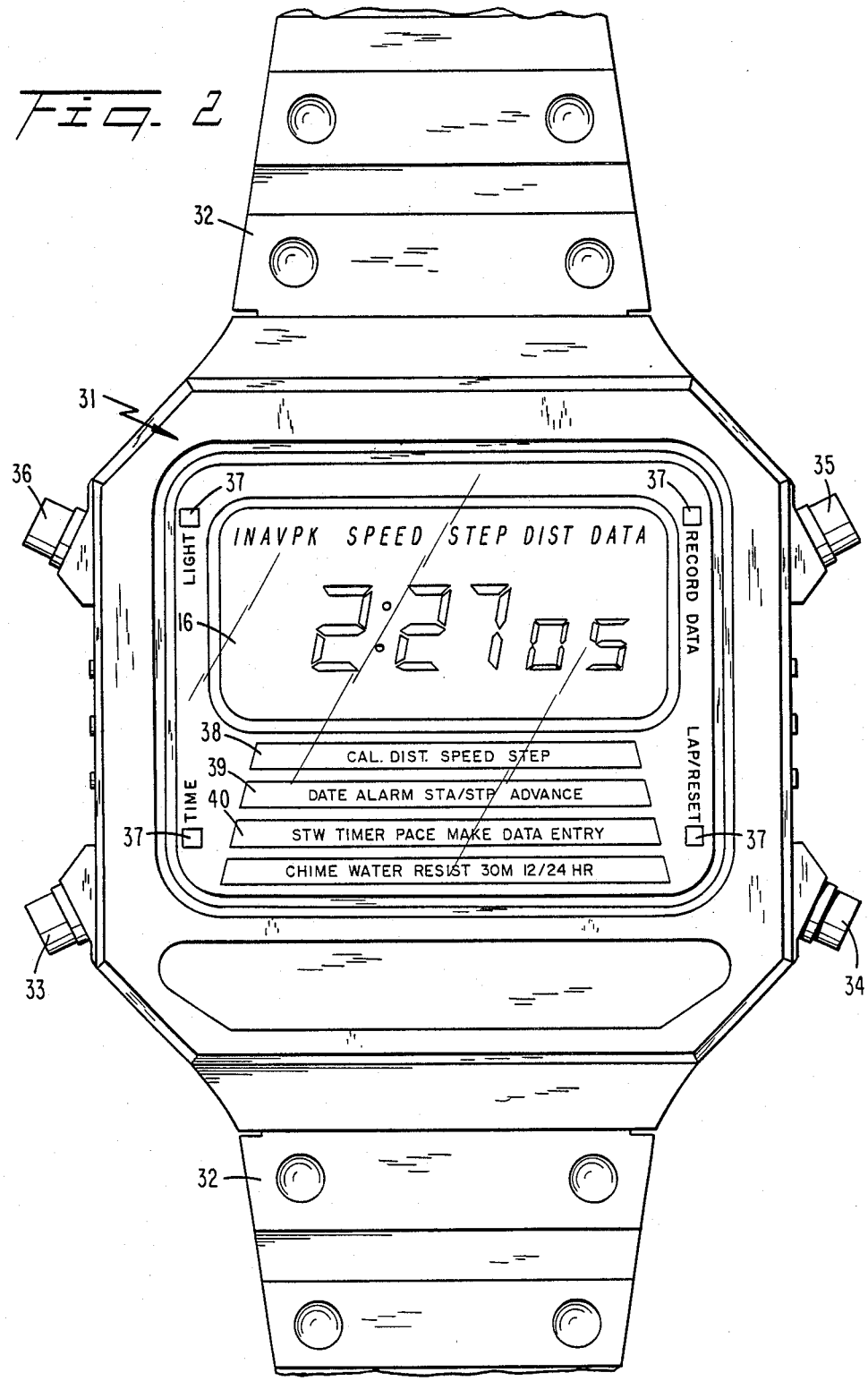

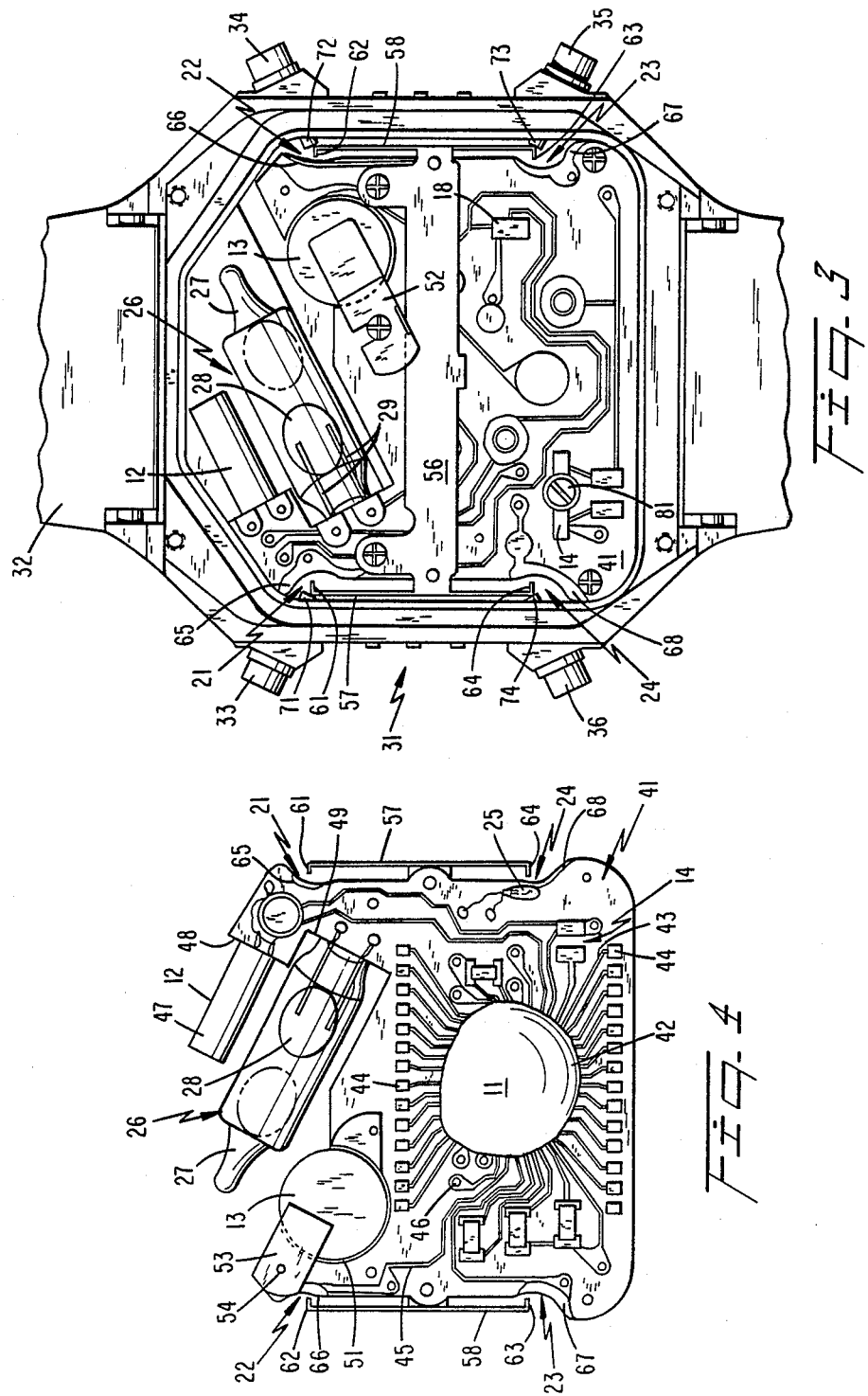

PEDOMETER AND/OR CALORIE MEASURING DEVICE AND METHOD

FIELD OF INVENTION

The present invention relates generally to devices for determining the number of cycles taken by a cyclically moving member and more particularly to such a device including a mercury switch having a mercury globule which functions as an inertia member to open and close contacts of the switch in response to cyclic movement of the member; this aspect of the invention has particular relevance to pedometers. In accordance with another aspect of the invention, calories consumed by a subject are determined in response to indications of distance travelled by the subject during a predetermined time interval multiplied by a factor determined by the weight of the subject.

BACKGROUND ART

There is disclosed in the commonly assigned U.S. Pat. No. 4,367,752, a device for determining, during an exercise routine, distance traversed by a subject, a fitness factor for the subject, and the number of calories expended. In the prior art device a case adapted to be mounted on the waistband or belt of a subject includes a mechanical switch having a pair of contacts, one of which includes an inertia member formed as a weight. In response to each step of the subject the switch contacts open and close, causing a pulse to be supplied to electronic circuitry including a computer. A heart rate monitor, preferably in the form of an electrode carrying chest band, is connected to the circuitry to supply the computer with a pulse in response to each heart beat of the subject. The case includes a keyboard with numeric (0-9) and function keys enabling the age, weight, stride length and gender of the subject to be entered into the computer.

The computer responds to the inputs supplied to it to derive a fitness factor. From the fitness factor an indication of calories consumed is derived. In the prior art device calories are therefore a function of heart rate, number of steps taken, stride length, age of the subject, sex of the subject, weight of the subject, fitness of the subject and the duration of the exercise routine. A liquid crystal display responds to commands from the keyboard and signals calculated and stored by the computer to provide the subject with numeric values for the fitness factor and calories consumed, as well as distance travelled, speed and duration of the exercise interval.

While the prior art device functions very satisfactorily, it has certain disadvantages, related particularly to case size, as well as inconvenience in case mounting and placing the chest band on the subject. The case of the prior art device is fairly large, being approximately 2½ by 4½ inches, and has a thickness of approximately ¾ of an inch. This size is necessary to accommodate the mechanical switch, the multikey keyboard and the relatively large liquid crystal display. A lead is connected between the chest band electrodes and the case to couple electrocardiogram signals from the electrodes to the electronic circuitry for processing into heart rate signals.

It is accordingly an object of the invention to provide a new and improved device for indicating the number of cycles taken by a cyclically moving member.

A further object of the present invention to provide a new and improved electronical pedometer and/or calorie measuring device.

Another object of the invention is to provide an electronic pedometer employing a switch that is very compact and which can fit into a small case, such as a wrist watch case.

An additional object of the invention is to provide a new and improved device for and method of indicating the number of calories expended by a subject in response to input signals representing distance traversed and weight of the subject, without being responsive to a heartbeat rate indication.

A further object of the invention is to provide a device for indicating the distance a subject has walked, jogged or run and the number of calories consumed while walking, jogging or running, which device is sufficiently small to be included as an integral part of an electronic wrist watch.

A further object of the invention is to provide a wrist watch having three data entry keys and a sensor for the movement of an arm of a subject wearing the watch wherein the watch has a display for indicating distance traversed, calories consumed and parameters concerned with the speed at which the distance was traversed.

A further object of the invention is to provide a wrist watch having three buttons for data representing the age, weight and sex of the wearer, as well as a sensor for the number of steps taken by the wearer and a computer for activating a display for the aforementioned parameters, as well as for distance traversed, number of steps taken, calories burned and speed parameters.

DISCLOSURE OF THE INVENTION

In accordance with one aspect of the invention a device adapted to be mounted on a cyclically moving member, e.g., a human body extremity, includes a mercury switch having a mercury globule that makes contact with and breaks contact away from a pair of contacts each time the extremity moves through a complete cycle. The mercury globule functions as an inertia member to provide bounceless contact between the mercury globule and the contacts in response to each cycle of movement. The contacts are connected to electric circuit means which generates a pulse each time the mercury globule moves through a make-break cycle. The number of pulses is directly proportional to the number of cycles of movement of the member; in the pedometer application, the number of pulses is directly proportional to the number of steps taken by a subject. In the preferred embodiment, one make-break cycle between the globule and electrodes occurs in response to every other step of the subject, whereby the number of pulses is equal to one-half of the steps taken by the subject The pulse generator is connected to or is a part of a programmed microcomputer included in the case. The computer includes a memory having stored therein an indication of subject stride length. The stride length indication and the output signal of the pulse generator are combined to derive an indication of distance traversed by the subject during a walking, jogging or running exercise routine.

For greatest accuracy, the watch is worn on the left arm, slightly above the wrist, and the forearm is maintained as close as parallel to the ground as possible, as is done by efficient walkers, joggers and runners. With the watch case worn in the usual position, so that the face of the watch is on the outside of the forearm, an envelope of the mercury switch is positioned in the case so its longitudinal axis is disposed approximately 30 degrees from the horizontal. The bottom of the envelope, where the switch contacts are located, is positioned toward the subject while the forearm is extended forward of the subject. In this position of the forearm and watch, the mercury globule normally bears against the bottom surface of the envelope, to bridge the contacts. The mercury globule bridges and connects the contacts at all times while the forearm is cyclically moving back and forth, except immediately after the forearm has reversed direction after its extreme forward movement. Because of the mercury globule mass and the position of the envelope and contacts the globule momentarily moves away from the contacts immediately after the forearm has reversed direction. While 30 degrees from the horizontal has been found to be a most advantageous position for the mercury globule to travel along, approximately the same results can be attained if the envelope longitudinal axis is displaced from the horizontal by 30 degrees plus or minus 15 degrees.

In accordance with a further aspect of the invention, calories are determined for certain activities, such as running, jogging or walking, in response to signals indicative of distance traversed, and parameters of the subject, principally subject weight. The calorie determination is made without an input from a heart rate monitor. Calories are preferably calculated in response to an input from a pedometer, as well as preset inputs indicative of subject age, weight and sex. During each of several computer computation periods the pedometer signal is combined with the subject preset inputs to determine the amount of energy exerted by the subject over the actual distance traversed relative to the energy expended by the subject in traversing a predetermined distance. The energy exerted by the subject over each computer computation period is accumulated to determine the energy, and therefore, calories consumed by the subject while performing the exercise routine.

Calories are determined from a approximately linear relationship of the number of calories burned by a subject having a known weight moving, by walking, jogging or running, through a predetermined distance having a net elevation change. Since a subject generally begins and ends an exercise routine involving walking, jogging or running at the same place, it is valid to assume that the net elevation change during the routine is zero. The linear relationship between calories burned and weight can be approximated as:

$$y = mx + b$$

where y equals calories burned by the subject moving through the predetermined distance x equals the weight of the subject, and m and b are predetermined constants. Because of energy efficiency gender differences in traversing the predetermined distance, the values of m and b differ for men and women. Hence, calories, $y_1$ and $y_2$, burned by men and women traversing the predetermined distance are represented by:

$$y_1 = m_1 + b_1 \tag{2a}$$

$$y_1 = m_2 x + b_2 \tag{2b}$$

where $m_1$, $b_1$ are predetermined constants for men, and $m_2$, $b_2$ are predetermined constants for women.

Because subject basil metabolism decreases with increases in age the number of calories burned by a subject walking, jogging or running through the predetermined distance decreases as age increases. For men, basil metabolism decreases by one-half of one percent for each year over 26; for women, basil metabolism decreases by one-half of one percent for each year over 21. In consequence, Equations (2a) and (2b) are adjusted as a function of age so the values of $y_1$ and $y_2$ are modified to:

$$y_1 = (m_1 x + b_1)(1 - 0.005(z - 26)) \tag{3}$$

for men having an age of 26 years or more, where z = the age of male subjects of age at least 26 years;

$$y_1 = m_1 x + b_1 \tag{4 for male subjects under age 26;}$$

$$y_2 = (m_2 x + b_2)(1 - 0.005(z - 21)) \tag{5}$$

for women 21 years or older, where z = the age of female subjects at age at least 21 years;

$$y_2 = m_2 x + b_2 \tag{6}$$

for female subjects under age 21.

Equations (3)–(6) indicate of the number of calories consumed by men and women of any age and weight by walking, jogging or running through a predetermined distance. The predetermined distance is one of the factors in determining the values of the constants $m_1$, $m_2$, $b_1$, and $b_2$. Because digital computers work most conveniently on a time, rather than distance basis, it is preferable to convert Equations (3)–(6) into equations relating distance traversed by the subject through a predetermined time interval. This conversion is made by determining the distance the subject traverses during the predetermined time interval, which is calculated by multiplying the number of steps (p) taken by the subject during the interval and the stride length (q) of the subject. The determined distance is divided by a constant (k) related to the length of the predetermined distance for which Equations (3)–(6) are applicable and the length of the predetermined time interval over which the distance is being determined. Hence, to determine the number of calories burned by a subject during each computer calculation interval the quantity computed from the right-hand side of each of equations (3)–(6) is multiplied by pq/k.

For each subject, the values of x (weight), z (age), sex and q (stride length) are entered into a memory of the computer before the subject begins to walk, jog or run. In response to the sex entry, the computer retrieves the values of $m_1$, $b_1$ or $m_2$, $b_2$. In response to the age and sex entries, the computer determines the metabolic factor for the subject as 1, (1 − 0.05(z − 26)) or (1 − 0.05(z − 21)). From the age, weight and sex entries, the value of $y_1$ or $y_2$ is determined from Equations (3)–(6) by the computer. From the stride length entry q, and the values of y and k the computer calculates a factor R, for the subject prior to the exercise routine beginning.

The factor R is stored in the computer memory and relates the number of strides taken by the subject during a computer calculation interval to the number of calories burned by the subject in moving through the predetermined distance. Hence, during operation, the computer, once having determined and stored the value of R for the subject, determines calories by multiplying the stored value of R for the particular subject by the number of steps taken by the subject during the computer interval. The thus computed products are accumulated by the computer over the duration of the exercise routine. The computer needs a relatively small amount of memory, need not store any cumbersome look up tables which require significant memory space, and need not perform cumbersome calculations during the exercise routine.

It has been found that calories are determined in response to the stated variables in an accurate manner for the walking, jogging and running routines. The calculation of calories based upon indications of number of steps, stride length, age, weight and sex is not as accurate as the calorie calculation achieved with a heart rate monitor. However eliminating the heart rate monitor enables the device of the present invention to be used more readily and conveniently than the prior art structure described in the aforementioned patent.

In a preferred embodiment, the apparatus of the present invention is mounted in a wrist watch having no external connections. The wrist watch includes a mercury switch pedometer, a microcomputer, a liquid crystal digital display and three buttons, in different corners of the watch. The buttons enable entry into the computer memory of data associated with subject age, weight, stride length and sex and to control readout from the computer to the liquid crystal display. The display is responsive to calculated values of calories, number of steps taken by the subject, distance travelled by the subject, average speed of the subject, instantaneous subject speed and peak subject speed, as well as the usual displays of a sports watch, i.e., time of day, day and month, stop watch indications and count down indications, as well as lap timing. The watch also includes a piezoelectric crystal beeper which can be activated to indicate each step taken by the subject, as well as for pacing purposes, and the usual alarm functions of a sports wrist watch.

It is, accordingly, a further object of the invention to provide a new and improved sport wrist watch.

Another object of the invention is to provide a sport wrist watch with a built in, bounceless pedometer electronic switch for enabling the watch to indicate various parameters associated with an exercise activity.

A further object of the invention is to provide a new and improved sport wrist watch including an electrically activated bounceless pedometer switch causing pulses to be supplied to a computer indicative of the number of steps taken by a subject, wherein the watch supplies a display with signals indicative of the number steps taken by the subject, the number of calories consumed by the subject, and the average, instantaneous and peak speeds of the subject during an exercise routine.

Still another object of the invention is to provide a new and improved electronic sport watch having a bounceless electronic, built in pedometer switch and only three data input buttons for enabling indications of subject weight, stride length, age and sex to be entered into a computer memory contained in the watch, as well as for enabling the usual functions associated with a sports watch to be entered into and performed by the sports watch.

The above and still further objects, features and advantages of the present invention will become apparent upon consideration of the following detailed description of one specific embodiment thereof, especially when taken in conjunction with the accompanying drawings.

BRIEF DESCRIPTION OF THE DRAWING

FIG. 2 is a plan view of the exterior of a sports watch in accordance with a preferred embodiment of the invention;

FIG. 3 is a plan view of the sports watch illustrated in FIG. 2, with the back face of the watch removed;

FIG. 4 is a plan view of the electronic printed circuit board illustrated in FIG. 3, from the reverse side;

DESCRIPTION OF THE PREFERRED EMBODIMENT

Figure 1:
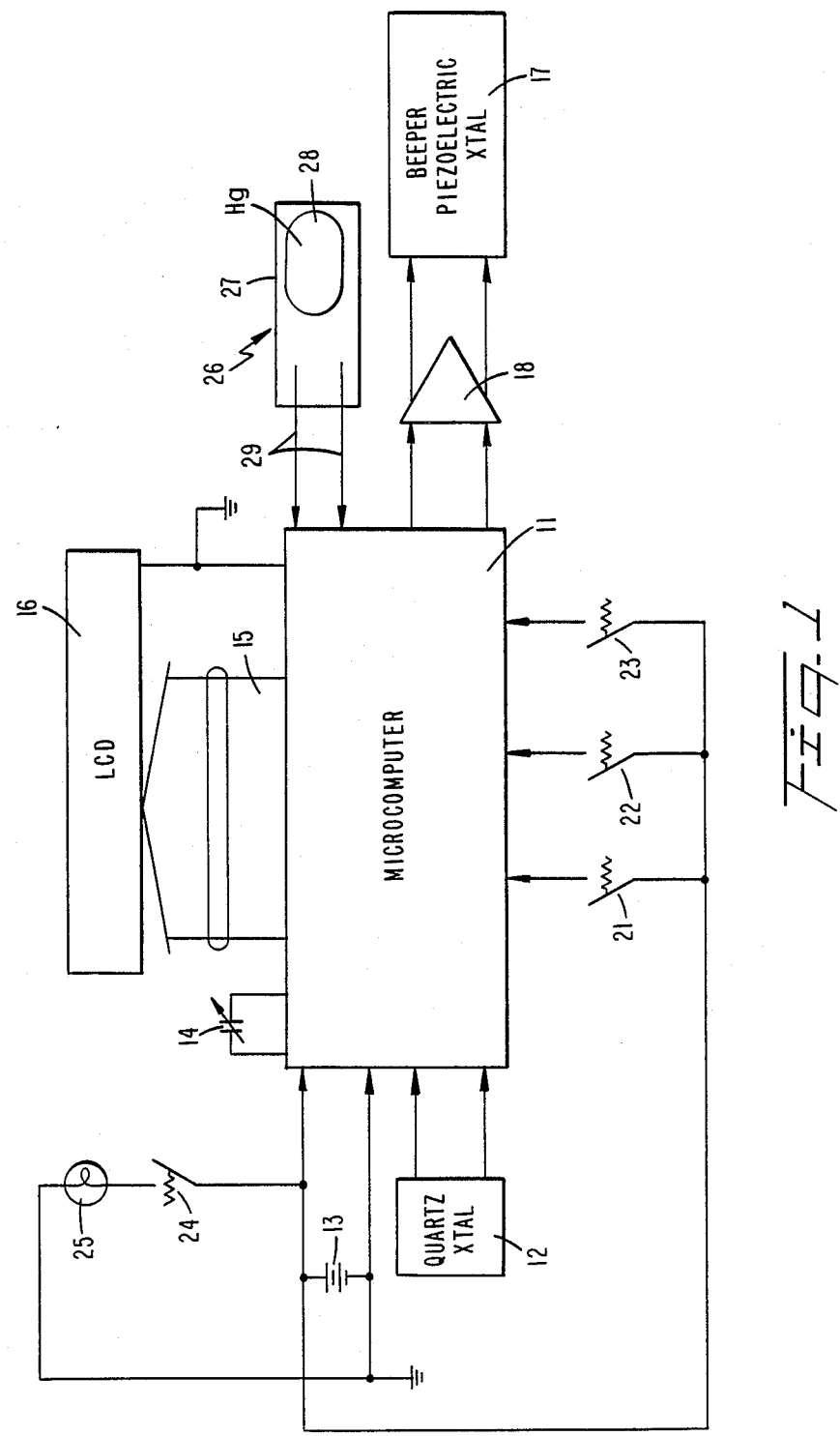
FIG. 1 is a circuit diagram of a preferred embodiment of the present invention.

Reference is now made to FIG. 1 of the drawing wherein there is schematically illustrated digital microcomputer 11, of the type employed in modern multifunction electronic sport watches. Microcomputer 11 includes a microprocessor, a read only memory (ROM) for storing program and display instructions and a random access memory (RAM) for storing at designated addresses data signals supplied to the microcomputer and values computed by the computer. The microprocessor in microcomputer 11 includes the usual elements, i.e., an input/output buffer, a central processing unit and clock circuitry including an oscillator responsive to quartz crystal 12. Microcomputer 11 and the remaining circuitry illustrated in FIG. 1 are powered by battery 13 of the type usually employed in electronic watches. The frequency of the oscillator in microcomputer 11 is controlled by crystal 12, as well as by the capacitance of variable capacitor 14, connected to the microcomputer.

Microcomputer 11 includes a multibit output bus 15 for supplying alpha-numeric representing digital signals to liquid crystal display 16. Liquid crystal display 16 is fabricated in the normal manner, but includes alpha and numeric indications associated with the age, weight, sex, and stride length of the subject, as well as indications of the number of steps taken by the subject during a walking, jogging or running exercise routine, the average speed of the subject during the exercise routine, the peak speed, instantaneous speed and calories consumed by the subject during the exercise routine. In addition, liquid crystal display 16 includes the usual displays associated with a sport watch, i.e., time of day, day and month, stop watch functions, lap timer, and countdown functions. Microcomputer 11 also supplies signals to beeper piezoelectric beeper crystal 17 by way of driver 18. Crystal 17 provides an aural signal to the subject every other time the subject takes a stride while the watch is in the stop watch operating mode. In addition, computer 11 can periodically supply a pacing signal to crystal 17, i.e., to provide the subject with a aural signal each time he should take a stride to maintain a particular speed or cadence in walking, jogging or running. Microcomputer 11 also supplies signals to beeper crystal 17 for the usual alarm and countdown functions of an electronic sports watch.

To enter data into microcomputer 11, switches 21–23 are provided. Switches 21–23 are normally spring biased to an open state, and are selectively closed by the subject pressing them in the usual manner of operating a sports watch. One contact of each switches 21-23 is connected in parallel to the positive electrode of battery 13, while the remaining contacts of the switches are connected to separate input terminals of microcomputer 11. The electronic watch of the present invention includes a fourth normally open spring biased switch 24, connected between lamp 25 and the electrodes of battery 13. Lamp 25 is mounted in proximity to liquid crystal display 16, to illuminate the display in response to switch 24 being closed by the user. Switches 21-24 are located in the four corners of the watch, in the usual manner. The nomenclature for switches 21-24 are respectively "TIME", "LAP/RESET", "RECORD DATA" and "LIGHT".

In response to switches 21-23 being closed different command signals are supplied to microcomputer 11. The read only memory of the microcomputer responds to depression of the buttons in the usual manner to derive control signals for liquid crystal display 16. However, the program is different from those usually included in microcomputer sports wrist watches to enale calculation of the various functions associated with calculation of calories and subject speed. Basically, switch 21 is closed to enable the subject to select the type of data to be entered into the random access memory of microcomputer 11. Closure of switch 23 causes numeric values to be entered into the random access memory at addresses controlled by the read only memory. In general, a numeric value is incremented by a count of one each time switch 23 is closed. However, if switch 23 is closed for in excess of a predetermined time interval, such as one or two seconds and remains so depressed, the numeric indication and liquid crystal display 13 are incremented at high speed in response to pulses from the oscillator responding to crystal 12 until switch 23 is open.

To provide the pedometer function, mercury switch 26 is mounted in the watch case. Mercury switch 26 includes a dielectric, preferably glass, envelope 27, a mercury globule 28 inside of envelope 27, and a pair of contact leads 29 extending through the bottom of envelope 27 into the interior of the envelope, to be wetted and bridged by globule 28. Mercury switch 26 is positioned in the watch casing so that in response to each swing of the left arm of a subject maintaining the arm parallel to the ground, the globule moves from a position, at the bottom of envelope 27, where it short circuits leads 29, to a position adjacent the top of the envelope, where the globule does not wet the contact leads, whereby the leads are open circuited.

Mercury globule 28 functions as an inertia member to provide bounceless closure of leads 29 each time the arm of the subject moves through one cycle. Since the arm is moved through a cycle each time the subject takes two steps, the number of times contacts 29 are opened is directly proportional to the number of steps taken by the subject. Bounceless closure of leads 29 is provided by mercury globule 28 because mercury has very high internal cohesive forces, such that the mercury remains in globular form and does not separate into droplets.

Contact leads 29 of mercury switch 26 are connected to circuitry in microcomputer 11 which generates a pulse each time the contacts are opened by mercury globule 28 moving away from them. Thereby, the circuitry within microcomputer 11 derives a pulse each time the left arm of the subject completes one movement cycle. The pulses derived in the microcomputer in response to contact leads 29 being open circuited from mercury globule 28 are counted during each cycle time of the computer. A signal indicative of the number of counted pulses during each computer cycle time is stored in a designated RAM address. The stored count indicative of number of counted pulses is combined with preset signals stored in the computer indicative of subject stride length to provide the pedometer function, and with the computer computation cycle time to derive the aforementioned speed parameters. The pulses generated by the circuitry responsive to opening of contacts 29 are also combined with the subject stride length indications, the subject weight indications, the subject sex indication and the subject weight indication to derive an indication of calories consumed.

Reference is now made to FIG. 2 of the drawing, a plane view of the exterior of a watch in accordance with a preferred embodiment of the invention. As illustrated in FIG. 2, the watch includes a plastic, dielectric relatively thin case 31 having a generally square outline. Secured to opposite edges of case 31 is strap 32 for enabling the watch to be placed around the wrist of a subject, in the normal fashion. In the four corners of case 31 are spring biased push buttons 33-36 which, when pushed inwardly, respectively, close switches 21-24. Push buttons 33-36 are of the type normally employed on conventional electronic sports watches. Legends assigned to push buttons 33-36 are respectively "TIME", "LAP/RESET", "RECORD DATA", and "LIGHT", respectively color coded with dots 37 as orange, blue, amber and white.

Extending across the top of the watch face is liquid crystal display 16. Below display 16 are stripes 38-40 containing abbreviations for instructions associated with buttons 33-35, and color coded in the same manner as the buttons. Stripe 38 is color coded orange, to correspond with button 32, and bears the nomenclature "STW TIMER PACE MAKER ENTRY"; stripe 39 is color coded amber to correspond with push button 33, and bears the nomenclature "DATE ALARM STA/STP ADVANCE"; and stripe 40 is color coded blue, to correspond with button 34, and bears the nomenclature "CAL DIST SPEED STEP".

Reference is now made to FIGS. 3 and 4 of the drawing wherein there are respectively illustrated front and back faces of dielectric printed circuit board 41, mounted in watch case 31 so that the planar surfaces of the printed circuit board are parallel to the plane of the watch face containing liquid crystal display 16. As illustrated in FIG. 4, microcomputer 11 is surface mounted on the back face of printed circuit board 41, i.e., the face of the board adjacent liquid crystal display 16. Surface mounted microcomputer 11 is covered with protective, insulative coating 42. Leads 43, coated or plated on the back face of board 41, extend from microcomputer 11 to terminal pads 44, engaged by pins (not shown) connected to liquid crystal display 16.

On opposite faces of printed circuit board 41 are coated or plated leads 45 for supplying to microcomputer 11 power from battery 13 and signals from crystal 12, capacitor 14, switches 21-23, and mercury switch contacts 29. Leads 45, on opposite sides of printed circuit board 41, are connected to each other by plated through holes 46 in the printed circuit board. Leads 43 and 45 and plated through holes 46 are covered with a dielectric coating (not shown), as is conventional in the art. However, terminals 44 and portions of conductive lands forming switches 21-24 are not covered by the dielectric coating, so that pads 44 and the conductive lands can engage metal contacts to provide electric connections.

In FIG. 3 watch case 31 is illustrated as it is mounted on the left wrist or lower forearm of a subject while walking, jogging or running with the left forearm parallel to the ground. The face of circuit board 41 illustrated in FIG. 3 is adjacent the watch backing. In FIG. 4 the face of circuit board 41 is illustrated in the position where case 31 is mounted on the left wrist of a person walking, jogging or running with the forearm parallel to the ground; the circuit board face illustrated in FIG. 4 is adjacent the watch face.

As illustrated in FIGS. 3 and 4, longitudinal axis 46 of elongated envelope 27 of mercury switch 26 is disposed at an angle of 30° from the horizontal when the watch is worn on the left wrist with the left forearm parallel to the ground. To provide this result, longitudinal axis 46 is displaced 60° from the axis of wrist watch strap 32. Envelope 27 is mounted in watch case 31 so leads 29, at one end of the envelope, are below the end of the envelope where no leads are located when the watch is worn on the left wrist or forearm and the forearm is parallel to the ground. Thereby, when the left forearm is in a stationary position, parallel to the ground, mercury globule 28 wets and bridges contacts 29 to short circuit the contacts together. Globule 28 wets and bridges contacts 29 while the arm is cyclically moved, with the forearm remaining parallel to the ground, except immediately after the left arm has reversed direction immediately after being extended farthest in front of the body of the subject. The inertia of mercury globule 28 is such that at the time of arm reversal the globule moves forward relative to the rest of envelope 27, toward the top end of the envelope 27. At this time globule 28 is approximately at the position indicated by dotted lines 28' where the globule no longer wets and bridges contacts 29 so the contacts are not connected to each other. At all other times during the cyclic movement of the left forearm during a walk, jogging or running exercise routine, the inertia of globule 28 is such that the globule wets and bridges contacts 29.

In response to globule 28 moving off of contacts 29 once during each arm movement cycle, a pulse is supplied by mercury switch 26 to microcomputer 11, whereby the number of pulses supplied to the microcomputer is equal to one half the number of steps taken by the subject. Hence, each time a pulse is derived by mercury switch 26, which in essence forms a pedometer sensor, the subject has taken two steps; thereby the number of steps and pulses are directly proportional to each other. While 60° has been found to be an optimal angle between the longitudinal axes of envelope 27 and watch strap 32, this angle can vary considerably, by up to and even in excess of plus or minus 15°. It is important for the longitudinal axis of envelope 27 not to be located in the vertical or horizontal plane while the pedometer including switch 26 is worn by the subject because globule 28 will not serve as an inertia member in these positions. Therefore, the longitudinal axes of envelope 27 and strap 31 should not be in line with or at right angles to each other.

For component mounting convenience, metal can 47, containing crystal 12, is positioned immediately adjacent envelope 27, and the can and envelope longitudinal axes are parallel. Envelope 27 and can 47 are mounted on parallel or planar edges 48 and 49 of printed circuit board 41. Battery 13 is mounted on printed circuit board 41 in a cavity having arcuate side walls 51. The upper face of battery 13, constituting one electrode of the battery, engages metal, spring-like tab 52, while the lower battery face, which constitutes another electrode of the battery, abuts against metal tab 50, connected to the plated metal land 53 on a face of board 41. Land 53 is connected by metal plated through-hole 54 to leads on the opposite sides of printed circuit board 41, as illustrated in FIG. 3. Metal tab 52 is pivotally mounted by rivet 55 on metal strap 56 that extends in a direction at right angles to the longitudinal axis of strap 32 between opposite edges of printed circuit board 41; strap 56 is on the face of circuit board 41 illustrated in FIG. 3.

Tab 52 and strap 56 are connected to metal arms 57 and 58 that extend parallel to the longitudinal axis of watch strap 32 along opposite edges of printed circuit board 41. Arms 57 and 58 are integral with strap 56, being constructed as spring biased contacts having fingers 61-64 extending toward printed circuit board 41. Each of lands 65-68 is coated on both faces of printed circuit board 41 and includes a conducting plating along the edge of the circuit board opposite from fingers 61-64.

Fingers 61-64 respectively engage the portions of lands 65-68 on the edges of circuit board 41 in response to buttons 33-36 being pushed inwardly. Buttons 33-36 respectively include extensions 71-74 arranged so that extension 71 bears against a corner at the intersection of arm 57 and finger 61, extension 72 engages a corner at the intersection of arm 58 and finger 64, extension 73 engages a corner at the intersection of arm 58 and finger 63, and extension 74 engages a corner at the intersection of arm 57 and finger 64. In response to buttons 33-36 being pressed inwardly, switches 21-24 are closed by virtue of the contact between finger 61 and land 65, between finger 62 and land 66, between finger 63 and land 67, and between finger 64 and land 68. In response to buttons 33-36 being released, the spring bias of arms 57 and 58 opens contacts 21-24 and pushes buttons 33-36 outwardly. In response to buttons 33-35 being depressed, current respectively flows from one electrode of battery 13 through tab 32 and strap 56 to fingers 61-63, thence to lands 65-67 and plated leads 45 on printed circuit board 41 to input terminals of computer 11. In response to button 36 being pushed, current flows from battery 13 through tab 52 and strap 56 to finger 64, thence to land 68 and bulb 25 to illuminate liquid crystal display 16.

To provide fine tuning for the oscillator in microcomputer 11, including quartz crystal 12 and variable capacitor 14, the value of the capacitor is adjusted by turning screw 81, which controls the value of the dielectric between electrodes of capacitor 14 in a manner well known to those skilled in the art. At the time of initial installation, the assembler turns screw 81 until the quartz crystal oscillator is at the correct, predetermined frequency for time-keeping purposes.

Figure 5:
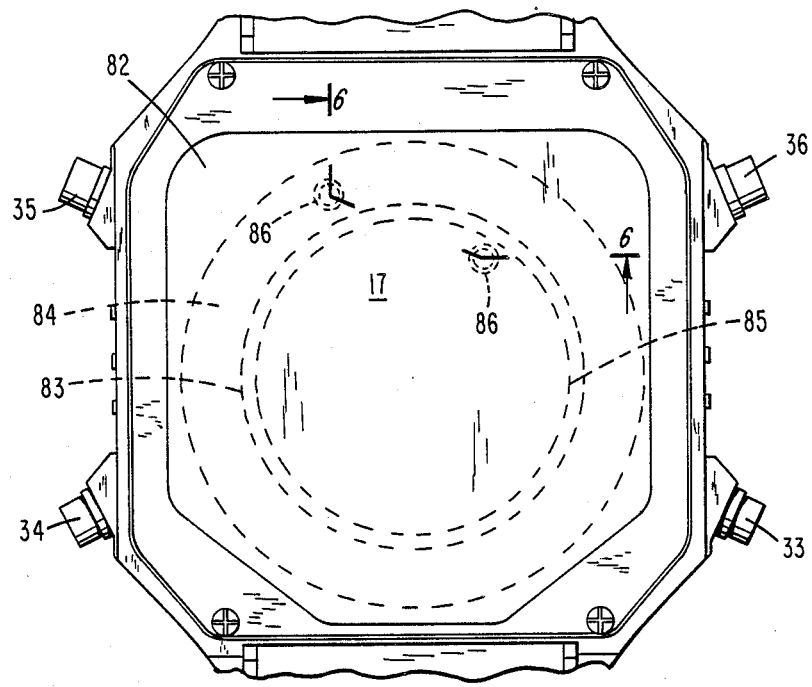
FIG. 5 is a plan view of the watch backing including a piezoelectric beeper slab.
Figure 6:
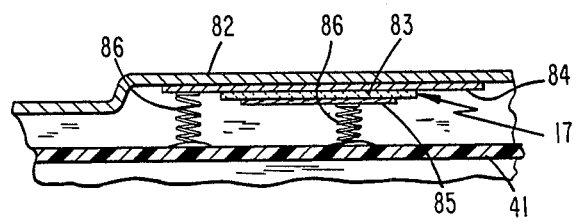
FIG. 6 is a side sectional view of the watch backing and connections between the piezoelectric slab and printed circuit board.

Piezo-electric crystal 17 is formed as a coating on stainless steel watch backing 82, FIGS. 5 and 6. Crystal 17 includes piezo-electric slab 83 that is deposited on aluminum coating 84, in turn deposited on backing 82. Aluminum coating 85 is applied to the face of slab 83 opposite from coating 84, whereby coatings 84 and 85 form electrodes on opposite faces of slab 83 for crystal 17. Electrical and mechanical contact is made between electrodes 84 and 85 and leads on printed circuit board 41 through metal compression springs 86 and 87 that respectively bear against coatings 84 and 85 and are connected to leads on printed circuit board 41.

The ROM and RAM in microcomputer 11 activate liquid crystal display 16 in the conventional manner in response to closure of switches 21–23 for the usual sport watch functions, namely display and adjustment of time, date, countdown timer, alarm timer and stopwatch. In response to pulses from the pedometer comprising mercury switch 26 and timing signals from the oscillator including quartz crystal 12 and input signals from switches 21–23, the ROM and RAM of microcomputer 11 are arranged to derive digital signals which are supplied to liquid crystal display 16 to indicate the instantaneous speeds of the subject during an exercise period, the average speed of the subject during the exercise period, the total distance traveled by the subject during the exercise period, the number of steps taken by the subject during the exercise period and the number of calories burned by the subject during the exercise period. All of these functions are performed while microcomputer 11 is operating in the stopwatch mode.

Prior to calculating instantaneous, peak and average speeds, total distance traveled and calories, push button 35 is pressed until the indicia "DATA" appear in the upper right-hand corner of the liquid crystal display. In the normal, clock mode, the indicia "INAVPK SPEED STEP DIST and DATA" appear on the upper line of the liquid crystal display. In response to button 33 being pressed in sequence four times, causing switch contacts 21 to close four times, display 16 is activated by the ROM so the bottom line of the liquid crystal display reads (1) "STW" (for stopwatch), (2) TMR (for countdown timer), (3) nothing i.e., there are no alpha numeric characters on the bottom line of the liquid crystal display, and (4) nothing. In response to the fourth activation of button 33, "DATA" appears in the upper right-hand corner of the display.

When the "DATA" indicia appear on the upper line, the program in the ROM addresses the RAM to read out ROM signals to the buffer so the center line of the liquid crystal display is activated to read either "0" or "1" (stored in a designated RAM address) followed by the letters "UT" (signals for "UT" are stored in a designated ROM address). The numeric values 0 and 1 followed by the letters "UT" signify whether distance, weight and speed data entries via button 34 and numeric values on display 16 are to be in metric or English units; 0=metric and 1=English. To change from English to metric units and vice versa, button 35, associated with contact 22, is pressed. In response to button 35 being pressed with the read only memory causing display 16 to be in state (4) a designated RAM address changes state from one to zero and vice versa.

The sex of the subject may then be changed by pressing button 34, closing switch contact 23. This causes the program in the ROM to access designated addresses in the RAM and ROM to cause a "0" or "1" value to appear on the middle line of the liquid crystal display followed by the letters "SE"; 0=female and 1=male. To change the sex from male to female, button 35 is pressed, causing the designated RAM address to change state. In response to the designated RAM address indicating that the subject is a female, designated ROM addresses for female coefficients are read out to the arithmetic logic unit (ALU) of the computer during a computation interval for the subject calorie factor; other designated ROM addresses are read in response to the sex designated ROM address having a value associated with a male subject.

Button 34 is then pressed to set the age of the subject, so that the program in the ROM reads out designated RAM and ROM addresses to cause the display center line to display a numeric value followed by "AE". To change the age of the subject stored in the RAM designated address, button 35 is pressed. To increment age by a count of one, button 35 is pressed instantaneously and released. If, however, it is desired to change the age value significantly, button 35 is pressed for in excess of two seconds and remains pressed until a value slightly less than the age of the subject is displayed on display 16, at which time button 35 is released. Button 35 is then depressed and released for short intervals until the desired subject age numeric value is reached value in the center line of liquid crystal display 16. In the preferred embodiment, the age sequences through a range from 5 through 99 years.

After the age of the subject has been set, button 34 is again pressed, causing the program in the ROM to address the RAM and ROM so the center line of display 16 displays a numerical value followed by the letters "WT" for weight change entries. The display numerical value is then incremented by pressing button 34, for either step by step or high speed changes, as described in connection with the age display. The weight values can be set anywhere from 50 through 500 pounds, or 22 through 227 kilograms, depending upon whether a display 16 has been set to 1 or 0 while "UT" appeared in the center line.

Next, button 35 is pressed, causing the program in ROM to address the RAM and ROM so the center line of display 16 has a numerical value, followed by the letters "SL", enabling stride length of the subject to be entered. The stride length is entered by depressing button 34, as described for the age setting. The stride length in the preferred embodiment, can be set anywhere from 30 to 200 centimeters, or 13 to 84 inches.

After stride length has been entered, button 33 is pressed, causing time of day to be displayed again on the display center line.

Each time button 35 is depressed while the "AE", "WT", and "SL" indicia are displayed on the center line of the liquid crystal display while "DATA" is displayed in the upper right-hand corner of the display, a pulse is supplied by the oscillator including crystal 16 to the input of microcomputer 11. Each pulse increments by a count of one, count values stored in three different addresses in the microcomputer RAM respectively associated with age, weight and stride length; the appropriate RAM address is accessed by the ROM being at the address associated with display of DATA and one of age, weight or stride length. In response to button 35 being pressed for in excess of two seconds while the program in the ROM is at an address causing DATA and AE, WT or SL to be displayed, a gate in microcomputer 11 responsive to pulses from the oscillator is opened to increment continuously the counts in the designated RAM addresses associated with age, weight and stride length. The center line of the liquid crystal display 16 responds, through an input/output buffer of microcomputer 11, to the RAM accessed address to display the numerical values for age, weight and stride length, in a manner known to those of ordinary skill in the art. Also, the designated RAM addresses are incremental in an accumulator register of microcomputer 11 in a manner well known to those of ordinary skill.

Microcomputer 11 responds to the sex, units, age, weight and stride length signals to compute periodically, preferably once every six seconds, signals having numeric values indicative of subject distance traveled during the period, subject speed during the period, peak subject speed since the stop watch mode was entered, average subject speed since the stop watch mode was entered and calories consumed since the stop watch mode was entered; the six second period is the computer cycle period.

The distance traveled during the period is computed by microcomputer 11 counting the number of pulses derived as a result of globule 28 moving from and open circuiting contacts 29 during the period and multiplying the number of pulses by twice the subject stride length. To this end, microcomputer 11 derives a pulse each time globule 28 moves from contacts 29 and derives a digital signal indicative of the number of pulses during each computer cycle period. The digital signal is derived in a manner known to those skilled in the art, as disclosed, e.g., in the aforementioned patent The digital signal indicative of the number of pulses is multiplied by two in the ALU and stored in a designated RAM address. At the end of the six second period, designated RAM addresses where stride length and the number of pulses are stored are addressed and supplied to the ALU. The microcomputer is programmed to multiply the number of steps by twice the subject stride length to derive an indication of distance traveled during the six second period. The stored indication of distance traveled is supplied to a designed RAM address to enable "instantaneous" speed to be calculated during the six second interval, to update average and peak speeds since the beginning of the exercise period (when the stop watch mode was entered) and to compute calories consumed during the six second interval.

"Instantaneous" speed during the six second period is the distance traveled during the period divided by the length of the time interval of the period. The computed value of instantaneous speed is supplied by the ALU to a RAM designated address under the control of the program stored in ROM. The designated address for instantaneous speed is updated after each six second interval.

The instantaneous speed signal is combined with the previous accumulated value of average speed, as stored at a designated RAM address. The previously accumulated value of average speed is combined in the ALU under the control of a sub-routine program stored in the microcomputer ROM in accordance with a known algorithm to compute average speed, as updated by the measurements taken during the previous six second interval. The thus computed average speed is returned to the RAM designated address under the control of the program stored in the ROM.

The instantaneous speed during the six second interval is compared in the ALU with the peak value signal stored in a designated RAM address. If the instantaneous speed during the just completed six second interval is greater than the peak value previously stored in the designated RAM address, the instantaneous value is returned to the designated address as a new peak value. If, however, the peak value previously stored in the designated RAM address exceeds the value during the previous six second interval, the stored value is returned to the designated RAM address.

Calories consumed during the previous six second interval are calculated by multiplying a previously determined factor R for the subject by the number of pulses generated during the six second calculation interval. For male subjects 26 years of age or older the value of R is calculated from Equation 3 as:

$$4.008 \times 10^{-7}(15x+642)(1-0.005)(z-26)q;$$

for male subjects under age 26

$$R = 4.0008 \times 10^{-7}(15x+642)q;$$

for female subjects 21 years of age or older, $$R = 4.008 \times 10^{-7}(14.76x+589)(1-0.005)(z-21)q,$$

for female subjects under 21 years of age $$R = 4.008 \times 10^{-7}(14.76x+589)q$$

where x is the weight of the subject in kilograms, q is the subject stride length in centimeters, and z is the age of a male subject 26 years of age or older and the age of a female subject 21 years of age or older.

The value of R is, in this instance, based upon Equations 1-6. The value of R is computed by microcomputer 11 in response to the values of units, subject age, weight, sex, and stride length initially entered into the microcomputer memory in response to activation of buttons, 33-35. The entered values of age (numeric) and sex (0 or 1) are logically combined in the ALU, to determine which expression for R, as stored in the ROM, is to be used. The subroutine associated with calculating R is entered in response to button 33 being pressed. The entered value of units (0 or 1) determines whether appropriate coefficient changes will be made in the ALU for the entered and read out values of distance, weight and speed.

The initially calculated value of R for the particular subject is stored in a designated RAM address and is read out into the ALU once during each computation cycle interval time. The value of R supplied by the RAM to the ALU is combined with a stored value for the number of steps taken by the subject (determined by counting the number of pulses generated in response to globule 38 opening contacts 29) during each cycle period to determine the number of calories consumed by the subject during the computer period. The calculated number of calories for the period is combined in the ALU accumulator register with a previous indication of number of total consumed calories computed during the exercise regime, as stored in a designated RAM address. The signal in the accumulator register is returned to the designated RAM address for total calories computed.

To read out the stored signals indicative of the number of steps taken during the exercise routine, peak speed during the exercise routine, distance traveled during the exercise routine, speed during the last computer period of the exercise routine, average speed during the exercise routine, and number of calories consumed during the exercise routine, button 35 is pressed after the routine has been completed. Pressing button 35 terminates the stopwatch operation. Button 33 is then pressed, causing the contents of the RAM address where time of day is stored to be displayed. Then, button 34 is pressed in sequence six times to provide sequential read out of the six aforementioned quantities.

In response to the first depression of button 34 the program stored in the ROM reads out the RAM address where number of steps is stored through the microcomputer input/output buffer to liquid crystal display 16; a maximum of 999,999 steps can be displayed. In response to the second depression of button 34, the contents of the RAM address where instantaneous speed is stored, which corresponds to the subject speed during the last six second calculation period, are supplied to display 16 via the microcomputer input/output buffer. In response to the next four depressions of button 34, the peak speed, average speed, distance and calorie indications stored in the designated random access memory addresses are sequentially supplied to display 16. Continued depressions of button 34 repeatedly sequence display 16 through the indications for number of steps, actual or instantaneous speed, peak speed, average speed, distance and calories consumed.

The microcomputer ROM stores signals to indicate what parameters are being displayed. Thereby, in response to the first depression of button 34 the program stored in the ROM addresses a designated ROM address to read out signals to display 16, causing the upper display line to read "STEP", in response to the second depression of button 34. The upper display line 16 responds to an address in the random access memory to provide indicia "IN SPEED", and the right side of the display middle line reads, either "M H" or "K H", depending upon whether a 1 or 0 was displayed while the display middle line read "UT". In response to the next two depressions of button 34, the display top line responds to designated ROM addresses to display indicia "PK SPEED", and "AV SPEED", while the ROM address causes the display middle line to read "MH" or "KH". In response to the fifth depression of button 34, the top display line responds to a designated ROM address to display "DIST", while the middle line of the display reads, on the right side, either "ML" or "KM". In response to the sixth depression of button 34, display 16 responds to a designated ROM address that causes the letters "CA" to be displayed on the center display line.

As an auxiliary subroutine, instantaneous speed and number of steps can be determined while the subject is performing an exercise routine, while the stop watch mode is entered. To these ends, the ROM is programmed so that in response to the computer being in the stopwatch mode, sequential depressions of buttons 35, 33 and 34 cause the upper display line to respond to a designated ROM address to display "STEP" while the display center line responds to a designated RAM address to indicate the number of steps taken prior to depression of button 35; depression of button 35 activates the computer into the "LAP TIMER" mode. The next depression of button 34 causes the top display line to respond to a ROM memory address that causes: the top line to read "IN SPEED", the center display line to read either "KH" or "MH", and the center display line to respond the RAM designated address where subject speed during the previous six second calculation interval is stored.

The pacer function involves providing the subject with a predetermined number of aural pulses; the number of pulses per minute is settable from 5 to 160 in 5 pulses per minute increments. To set the desired number of aural pulses or beeps per minute for pacing purposes, button 33 is activated three times from the time display, whereby the center display line is supplied with a number indicating signal from the RAM, followed by the letters "PM", as supplied to the display from a designated ROM address. The digital display is incremented in units of five each time button 34 is pressed for less than two seconds. In response to button 34 being pressed for more than two seconds the digital indicia on the display center line is incremented rapidly. Pressing button 34 sets a count down factor in a count down register of the microcomputer ALU. The count down register is responsive to pulses from the oscillator including crystal 12, to control the frequency of pulses supplied by the oscillator to beeper piezoelectric crystal 17 by way of amplifier 18. The countdown register setting is controlled by a designated RAM address loaded with pulses from the oscillator in response to pressing key 34 being pressed.

After the designated pacer pulse rate has been set and displayed on liquid crystal display 16, the pacer function is instigated by pressing button 33 while the watch is in the pacer mode. The ROM is programmed to respond to pressing of button 35 at this time by opening a gate in the microcomputer to supply pulses to amplifier 18 and crystal 17, causing aural pulses to be derived from the piezoelectric crystal at the designated pacer rate. After the pacer rate has been set, button 33 is pressed, to return display 16 to the time of day indication. The pacer beep function is activated by pressing button 34 and then pressing button 35. Each time button 3 is thereafter pressed causes the pacer beep to be either turned on or turned off. When the pacer beep is on the ROM activates display 16 so that in the lower right hand corner thereof a special pictorial representation appears.

Crystal 17 responds to pulses from microcomputer 11 to provide an aural beep in response to many different functions performed by the microcomputer; amongst these functions are: (a) sensing open circuiting of contacts 19, each time each of buttons 33–35 is pressed, responding to a count of zero being reached in the clock countdown mode, and responding to the time set for the alarm to go off being reached, provided that the alarm setting has been set.

While there has been described and illustrated one specific embodiment of the invention, it will be clear that variations in the details of the embodiment specifically illustrated and described may be made without departing from the true spirit and scope of the invention as defined in the appended claims.

I claim:

1. A method of measuring an approximate number of calories consumed by a subject performing an exercise routine, the method being performed with a computer having a predetermined cycle time, comprising the steps of determining distance travelled by the subject during the computer cycle time, entering an indication of weight of the subject into a memory of the computer, activating the computer to store an indication of the number of calories the subject burns in traversing a predetermined distance during the computer cycle time in response to the stored weight indication, calculating the calories consumed by the subject during the cycle time from the stored indication and the distance travelled during the cycle time, and accumulating the calculated consumed calories over several consecutive cycle times.

2. The method of claim 1 further comprising the step of entering an indication of the sex of the subject into the computer memory, and using the entered sex indication to calculate the calories consumed by the subject during the cycle time.

3. The method of claim 1 wherein the number, y, of calories burned in traversing the predetermined distance is calculated by the computer in accordance with $$y = mx + b$$

where m and b are predetermined constants, and x is the weight of the subject.

4. The method of claim 1 further including entering an indication of the sex of the subject into the computer memory, wherein the number of calories burned by male and female subjects in traversing the predetermined distance is calculated by the computer in accordance with $$y_1 = m_1 x + b_1, \text{ and}$$

$$y_2 = m_2 x + b_2$$

where:
$y_1$ and $y_2$ are respectively the number of calories burned by male and female subjects,
x = weight of the subject
$m_1$ and $m_2$ are different predetermined constants and $b_1$ and $b_2$ are different predetermined constants.

5. The method of claim 1 further including entering indications of the sex and age of the subject into the computer memory, wherein the number of calories burned by male and female subjects in traversing the predetermined distance is calculated by the computer in accordance with $$y_1 = (mx + b)(1 - 0.005(z - 26))$$

$$y_2 = (mx + b)$$

$$y_3 = (mx + b)(1 - 0.005(z - 21))$$

$$y_4 = mx + b$$

where
m and b are predetermined constants
$y_1$ and $y_2$ are respectively the number of calories burned by male subjects having ages above and below 25 years,
$y_3$ and $y_4$ are respectively the number of calories burned by female subjects having ages above and below 20 years,
x = weight of the subject.

6. The method of claim 1 further including entering indications of the sex and age of the subject into the computer memory, wherein the number of calories burned by male and female subjects in traversing the predetermined distance is calculated b the computer in accordance with $$y_1 = (m_1 x + b_1)(1 - 0.005(z - 26))$$

$$y_2 = (m_1 x + b_1)$$

$$y_3 = (m_2 x + b_2)(1 - 0.005(z - 21))$$

$$y_4 = m_2 x + b_2$$

where
$m_1$ and $b_1$ are predetermined constants for male subjects
$m_2$ and $b_2$ are predetermined constants for female subjects $$(m_1 \neq m_2), (b_1 \neq b_2)$$

x = weight of the subject.

7. The method of claim 1 further comprising the step of entering an indication of the age of the subject into the computer memory, and using the entered age indication to calculate the calories consumed by the subject during the cycle time.

8. The method of claim 7 wherein the entered age reduces the number of calories by a predetermined factor for every year of the subject over a predetermined age.

9. The method of claim 8 wherein the factor is 0.005.

10. The method of claim 7 further comprising the step of entering an indication of the sex of the subject into the computer memory, and using the entered sex indication to calculate the calories consumed by the subject during the cycle time.

11. The method of claim 10 wherein the entered age indication reduces the number of calories by a predetermined factor for every year of male subjects over the age of 25 and of female subjects over the age of 20.

12. The method of claim 11 wherein the factor is 0.005.

13. Apparatus for determining an approximate number of calories consumed by a subject comprising computer means, pedometer means coupled to the computer means for causing the computer means to derive a first signal indicative of number of steps taken by the subject in a unit length of time, switch means for supplying to the computer means electric signals indicative of subject stride length and subject weight, the computer means responding to the electric signals to derive a second signal indicative of a constant factor indicative of calories consumed by the subject traversing a predetermined distance during the unit length of time, the computer means responding to the first and second signals for deriving a third signal indicative of the number of calories consumed by the subject in each unit length of time and for accumulating the values of the third signals to derive a fourth signal indicative of total calories consumed by the subject, and display means responsive to the fourth signal.

14. The apparatus of claim 13 wherein the computer computes the number of calories consumed by the subject in traversing the predetermined distances in accordance with $$y = mx + b$$

where m and b are predetermined constants, and x is the weight of the subject.

15. The apparatus of claim 13 wherein the switch means supplies electric signals indicative of the sex of the subject to the computer, and the number of calories burned by male and female subjects in traversing the predetermined distance is calculated by the computer in accordance with $$y_1 = m_1 x + b, \text{ and}$$

$$y_2 = m_2 x + b_2$$

where:
  $y_1$ and $y_2$ are respectively the number of calories burned by male and female subjects,
  x = weight of the subject
  $m_1$ and $m_2$ are different predetermined constants and $b_1$ and $b_2$ are different predetermined constants.

16. The apparatus of claim 13 wherein the switch means supplies electric signals indicative of the age of the subject to the computer, wherein the number of calories burned by male and female subjects in traversing the predetermined distance is calculated by the computer in accordance with $$y_1 = (mx+b)(1-0.005(z-26))$$

$$y_2 = (mx+b)$$

$$y_3 = (mx+b)(1-0.005(z-21))$$

$$y_4 = mx+b$$

where
  m and b are predetermined constants
  $y_1$ and $y_2$ are respectively the number of calories burned by male subjects having ages above and below 25 years,
  $y_3$ and $y_4$ are respectively the number of calories burned by female subjects having ages above and below 20 years,
  x = weight of the subject.

17. The apparatus of claim 13 wherein the switch means supplies electric signals indicative of the sex of the subject to the computer, wherein the number of calories burned by male and female subjects in traversing the predetermined distance is calculated by the computer in accordance with $$m_1 = (mx+b)(1-0.005(z-26))$$

$$b_1 = (mx+b)$$

$$m_2 = (mx+b)(1-0.005(z-21))$$

$$b_2 = mx+b$$

where
  $m_1$ and $b_1$ are predetermined constants for male subjects
  $m_2$ and $b_2$ are predetermined constants for female subjects $$(m_1 \neq m_2), (b_1 \neq b_2)$$

x = weight of the subject.

18. The apparatus of claim 13 wherein the computer means, pedometer means, switch means and display means are mounted in a wrist watch case, the switch means being responsive to push buttons on the watch case.

19. The apparatus of claim 18 wherein the pedometer means includes a mercury switch including an envelope containing contacts and a mercury globule for selectively wetting and bridging said contacts in response to cyclic motion of an arm of the subject associated with walking, running or jogging so the contacts are bridged by the globule in response to alternate steps of the subject, the contact being connected to the computer so the computer generates a number of pulses directly proportional to the number of motion cycles of the arm.

20. The apparatus of claim 19 wherein the watch includes a strap for the forearm or wrist of the subject, the envelope having a longitudinal axis disposed at a predetermined angle relative to the strap axis, the contacts being disposed at one end of the envelope.

21. The apparatus of claim 20 wherein the angle is $60° \pm 15°$.

22. Apparatus for determining number of cycles taken by a member undergoing cyclic movement comprising a case to be mounted on the number so that it moves with the member, the case including a mercury switch including an envelope having contacts and a mercury globule for selectively wetting and bridging the contacts to selectively open and short circuit the contacts, the mercury globule being an inertial member, the case to be mounted on the member and the envelope being mounted in the casing so that in response to each cycle of the cyclic movement of the member the globule moves relative to the envelope and contacts to cause the contacts to be open and closed, and electric circuit means connected to the contacts for generating a first electric signal having a value indicative of the number of times the contacts change between open and closed circuit conditions, and display means responsive to the value of the first electric signal for displaying a value determined by the value of the first electric signal.

23. The apparatus of claim 22 wherein the apparatus is a pedometer, wherein the case is configured as a wrist watch case, a wrist strap having a longitudinal axis attached to the case, the envelope having a longitudinal axis, the contacts being at one end of the envelope, the strap and envelope longitudinal axes being displaced by $60° \pm 15°$.

24. The apparatus of claim 22 wherein the apparatus is a pedometer, wherein the case is configured as a wrist watch case, a wrist strap having a longitudinal axis attached to the case.

25. The apparatus of claim 22 wherein the apparatus is a pedometer, the case being adapted to be mounted on a limb of a subject whereby the limb comprises the member, the apparatus further including a battery connected to energize the electric circuit means, the battery and electric circuit means being mounted in the case.

26. The apparatus of claim 25 further including manually activated switch means mounted on the case for supplying the electric circuit means with second and third signals respectively indicative of subject weight and stride length, the electric circuit means responding to the second and third signals and opening and closing of the contacts for deriving a fourth signal indicative of calories consumed by the subject, the manually activated switch means being connected to the circuit means to selectively couple the value indicated by the fourth signal to the display means.

27. The apparatus of claim 25 further including manually activated switch means mounted on the case for supplying the electric circuit means with a second signal indicative of subject stride length, the electric circuit means responding to the second signal and opening and closing of the contacts for deriving a third signal indicative of distance traversed by the subject, the manually activated switch means being connected to the circuit means to selectively couple values indicated by the first and third signals to the display means.

28. The apparatus of claim 27 wherein the electric circuit means has a predetermined operating interval, the electric circuit means responding to the second signal and the number of contacts opening and closing during each operating interval for deriving a fourth signal indicative of the speed of the subject during the interval, the manually activated switch means being connected to the circuit means to selectively couple a signal responsive to the value of the fourth signal to the display means.

29. The apparatus of claim 28 wherein the electric circuit means responds to the value of the fourth signal over several of said intervals to derive a fifth signal indicative of the average speed of the subject over said several intervals, the manually activated switch means being connected to the circuit means to selectively couple a signal indicative of the value of the fifth signal to the display means.

30. Apparatus for determining an approximate number of calories consumed by a subject comprising computer means for deriving a first signal indicative of the number of steps taken by the subject in a unit length of time, switch means for supplying to the computer means electric signals indicative of subject stride length and subject weight, the computer means responding to the electric signals to derive a second signal indicative of a constant factor indicative of calories consumed by the subject traversing a predetermined distance during the unit length of time, the computer means responding to the first and second signals for deriving a third signal indicative of the number of calories consumed by the subject in each unit length of time and for accumulating the values of the third signals to derive a fourth signal indicative of total calories consumed by the subject, and display means responsive to the fourth signal.

31. The apparatus of claim 30 wherein the switch means supplied electric signals indicative of the age of the subject to the computer, the computer responding to the electric signals indicative of age as well as the signal indicative of number of steps taken per unit length of time and the electric signals indicative of stride length and subject weight for deriving the second signal.

32. The apparatus of claim 30 wherein the switch means supplies electric signals indicative of the sex and age of the subject to the computer, the computer responding to the electric signals indicative of sex and age as well as the signal indicative of number of steps taken per unit length of time and the electric signals indicative of stride length and subject weight for deriving the second signal.

33. The apparatus of claim 30 wherein the switch means supplies electric signals indicative of the sex of the subject to the computer, the computer responding to the electric signals indicative of sex as well as the signal indicative of number of steps taken per unit length of time and the electric signals indicative of stride length and subject weight for deriving the second signal.

34. The apparatus of claim 33 wherein the computer computes the number of calories burned by male and female subjects in accordance with:

$$y_1 = m_1 x + b_1, \text{ and}$$

$$y_2 = m_2 x + b_2$$

where:
$y_1$ and $y_2$ are respectively the number of calories burned by male and female subjects,
$x$ = weight of the subject
$m_1$ and $m_2$ are different predetermined constants and
$b_1$ and $b_2$ are different predetermined constants.

35. The apparatus of claim 30 wherein the computer means, switch means and display means are mounted in a wrist watch case, the switch means being responsive to push buttons on the watch case.

36. The apparatus of claim 35 wherein the switch means supplies electric signals indicative of the sex of the subject to the computer, the computer responding to the electric signals indicative of sex as well as the signal indicative of number of steps taken per unit length of time and the electric signals indicative of stride length and subject weight for deriving the second signal.

37. The apparatus of claim 35 wherein the switch means supplies electric signals indicative of the age of the subject to the computer, the computer responding to the electric signals indicative of age as well as the signal indicative of number of steps taken per unit length of time and the electric signals indicative of stride length and subject weight for deriving the second signal.

38. The apparatus of claim 35 wherein the switch means supplies electric signals indicative of the sex and age of the subject to the computer, the computer responding to the electric signals indicative of sex and age as well as the signal indicative of number of steps taken per unit length of time and the electric signals indicative of stride length and subject weight for deriving the second signal.

39. Apparatus for determining number of steps taken by a subject comprising a wrist watch case, the case including: a pedometer, switch means, display means and computer means; the pedometer including an inertial member having contacts positioned so that in response to every other step of a subject wearing the watch the contacts open and close, and means for connecting the contact means, switch means, computer means and display means to each other for selectively providing indications travelled by the subject of time and number of steps on the display.

40. The apparatus of claim 39 wherein the pedometer includes an envelope having contacts and a mercury globule for selectively wetting and bridging the contacts to selectively open and short circuit the contacts once each time the arm moves through a cycle as the subject takes a pair of steps.

41. Apparatus for determining distance travelled by a subject comprising a wrist watch case, the case including: a pedometer, switch means, display means and computer means; the pedometer including an inertial member having contacts positioned so that in response to every other step of a subject wearing the watch the contacts open and close, and means for connecting the contact means, switch means, computer means and display means to each other for selectively providing indication on the display of time and distance travelled by the subject.

42. The apparatus of claim 41 wherein the pedometer includes an envelope having contacts and a memory globule for selectively wetting and bridging the contacts to selectively open and short circuit the contacts once each time the arm moves through a cycle as the subject takes a pair of steps.

* * * * *